US006255541B1

(12) United States Patent
Paatero et al.

(10) Patent No.: US 6,255,541 B1
(45) Date of Patent: Jul. 3, 2001

(54) PROCESS FOR THE PREPARATION OF POLYVALENT ALCOHOLS

(75) Inventors: Erkki Paatero, Kauniainen; Esa Nummi, Lappeenranta; Lars Peter Lindfors, Espoo; Hannu Nousiainen; Jukka Hietala, both of Porvoo; Leila Lahtinen; Rami Haakana, both of Helsinki, all of (FI)

(73) Assignee: Neste Chemical Oy, Porvoo (FI)

( * ) Notice: Subject to any disclaimer, the term of this patent is extended or adjusted under 35 U.S.C. 154(b) by 0 days.

(21) Appl. No.: 09/319,572

(22) PCT Filed: Dec. 30, 1997

(86) PCT No.: PCT/FI97/00835

§ 371 Date: Jun. 9, 1999

§ 102(e) Date: Jun. 9, 1999

(87) PCT Pub. No.: WO98/29374

PCT Pub. Date: Jul. 9, 1998

(30) Foreign Application Priority Data

Dec. 30, 1996 (FI) ........................................ 965268

(51) Int. Cl.[7] ..................................... C07C 27/04
(52) U.S. Cl. ............................ 568/862; 568/863; 568/852
(58) Field of Search ..................... 568/862, 463, 568/464, 461; 502/164, 167; 260/635

(56) References Cited

U.S. PATENT DOCUMENTS 2,818,443  * 12/1957  Robeson ............................. 568/862
4,181,810     1/1980   Immel et al. .
4,233,247     11/1980  Immel et al. .
4,250,337     2/1981   zur Hausen et al. .
4,855,515     8/1989   Morris et al. .
5,475,154  * 12/1995  Lundquist et al. ................... 568/727

FOREIGN PATENT DOCUMENTS 1235883  3/1967   (DE) .
2653096  5/1978   (DE) .
2714516  5/1978   (DE) .
0343475  11/1989  (EP) .
0522368  1/1993   (EP) .
1143417  2/1969   (GB) .

* cited by examiner

Primary Examiner—Johann Richter
Assistant Examiner—Elvis O. Price
(74) Attorney, Agent, or Firm—Birch, Stewart, Kolasch & Birch, LLP

(57) ABSTRACT

The invention relates to a process for the preparation of polyvalent alcohols by hydrogenation of an aldehyde. According to the invention said aldehyde is obtained by aldolisation reaction of an aldehyde containing an α hydrogen atom and having the formula $R_1CHO$, or the mixture of said aldehyde with a second different aldehyde having the formula or $R_2CHO$, wherein $R_1$ is selected from alkyl having 1–12 carbon atoms, cycloalkyl, aryl and aralkyl having 1–14 carbon atoms, and $R_2$ is selected from H, alkyl having 1–12 carbon atoms, cycloalkyl, aryl and aralkyl having 1–14 carbon atoms, said aldolisation being carried out in the presence of a weak base anion exchange resin, and the hydrogenation being carried out in the presence of a solvent and a hydrogenation catalyst.

22 Claims, No Drawings

PROCESS FOR THE PREPARATION OF POLYVALENT ALCOHOLS

This application is the national phase under 35 U.S.C. §371 of PCT International Application No. PCT/FI97/00835 which has an International filing date of Dec. 30, 1997 which designated the United States of America.

The invention relates to a process for the preparation of polyvalent alcohols. More precisely, the invention relates to the preparation of polyvalent alcohols from aldehydes prepared by the aldolisation reaction and a subsequent hydrogenation reaction of said aldehyde to alcohols.

PRIOR ART

Neopentyl glycol and other corresponding alcohols are important intermediates, for example, in the production of various synthetic resins, such as acrylic resins, polyester resins, polyurethane resins, alkyd resins and polycarbonate resins. These alcohols are also used in the preparation of plasticizers, synthetic lubricants, surfactants, etc.

Neopentyl glycol and other corresponding alcohols have conventionally been prepared by two processes. In one process, formaldehyde and aldehyde are allowed to react with a strongly alkaline catalyst, such as sodium hydroxide, potassium hydroxide or calcium hydroxide, to form alcohol, such as neopentyl glycol. However, this process has the disadvantage that large amounts of corresponding formate are formed as a byproduct. Thus the process is not suitable for a commercial process, unless an economically profitable use is simultaneously found for the formate.

In the other process, the aldolisation reaction of formaldehyde and aldehyde is carried out in the presence of an amine catalyst, in particular triethylamine. Neopentyl glycol is obtained, for example, by reacting formaldehyde and isobutyraldehyde in the presence of triethylamine, whereby hydroxypivaldehyde is formed as the main product. This can further be hydrogenated, whereby the desired neopentyl glycol is obtained as the end product.

Many types of catalysts have been proposed as the hydrogenation catalyst. U.S. Pat. No. 4,250,337 proposes as the catalyst copper chromite with barium as its promotor. In U.S. Pat. No. 4,855,515, the catalyst used is a mixture of copper oxide and copper chromite, with manganese oxide as the promoter. In EP patent 343475, a mixed catalyst made up of platinum, ruthenium and tungsten is used as the catalyst.

Copper chromite alone is used as the catalyst in, for example, EP publication 522368. According to this publication, the quantity of byproducts formed in the aldolisation can be decreased in the hydrogenation by carrying out the hydrogenation in a suitable alcohol solvent, whereby the purity of the final neopentyl glycol can be increased.

The above-mentioned processes have various deficiencies. When triethylamine is used as the catalyst, the triethylamine is in a dissolved state in the reaction mixture and thus also present in the hydrogenation step, possibly catalyzing detrimental side reactions, thus reducing the yield of the desired alcohol. Triethylamine is a also a catalytic poison for many hydrogenation catalysts, which decreases the number of suitable catalysts that can be used. Further, triethylamine decomposes partly in the hydrogenation step increasing the catalyst consumption in the process. In order to minimize the catalyst consumption triethylamine must be separated after the hydrogenation by distillation from the reaction mixture obtained and be recycled to the hydrogenation and/or aldolisation reaction, which means one additional step in a continuous process.

Thus it would be beneficial if a catalyst of another type, which is not in a liquid form and will thus not end up in the reaction mixture going to hydrogenation, could be found to replace triethylamine, which is at present the most commonly used aldolisation catalyst. The investment costs of the entire process could thus be reduced, since a separate step for the separation of triethylamine from the hydrogenation product would not be necessary. Furthermore, many types of catalysts could be used in the hydrogenation without the catalyst poisoning caused by triethylamine and the consequent reduction of the conversion and/or the formation of byproducts.

The idea to use ion exchange resins as a catalyst in the aldolisation reaction is an old invention. U.S. Pat. No. 2,818,443 discloses a reaction of formaldehyde and an aliphatic aldehyde; containing at least two carbon atoms, in the presence of an anion exchange resin catalyst to form hydroxyaldehyde, which is further hydrogenated to the corresponding alcohol. In this patent it is noted that especially suitable anion exchange resins are resins containing quaternary ammonium groups, such as resins obtained by reacting tertiary amine with a copolymer of chloromethylated styrene and divinyl benzene. These resins are strong base anion exchange resins. It is also possible to use as the aldolisation catalyst a weak base anion exchange resin obtained by reacting dimethylamine with a copolymer of chloromethylated styrene and divinyl benzene.

According to this patent, the separation of unreacted formaldehyde from the reaction mixture before the hydrogenation is recommended. The separation is carried out by distillation under overpressure or by steam stripping under atmospheric pressure. The hydrogenation catalyst used according to this publication is Raney nickel.

DE patent 26 53 096 proposes the use of cation exchange resins as a catalyst for the aldolisation reaction. The aldolisation reaction can be performed in a suitable organic solvent, such as aliphatic alcohols. After the reaction, the cation exchange resin is removed by filtration, and any unreacted aldehyde is separated by distillation.

Recommended hydrogenation catalysts according to the patent are nickel- or cobalt-containing hydrogenation catalysts to which chromium, aluminum, magnesium, barium, zinc, manganese, thorium and/or copper has been added.

SUMMARY OF THE INVENTION

According to the present invention, it has been observed that by using weak base anion exchange resins as an aldolisation catalyst and by performing the hydrogenation of the aldolisation product in the presence of a solvent and a hydrogenation catalyst, many advantages are gained which are lacking in prior known processes.

The aldolisation reaction can be carried out with a good yield and without notable side reactions, especially the formation of esters. The selectivity of the process with respect to the desired alcohol increases. The aldolisation product can be fed directly to the hydrogenation step without any separation steps. No aldolisation catalyst, such as triethylamine, is present in the hydrogenation reaction, and thus its separation and recycling to the aldolisation step of the process is not necessary. Furthermore, it is possible in the hydrogenation step to use many kinds of catalysts without a triethylamine-catalyzed formation of byproducts and product purification steps related thereto. The hydrogenation can be carried out in milder conditions, because the use of solvent decreases considerably the temperature required enables reasonable low temperatures to be used in the hydrogenation step. Even temperatures below the melting point of the intermediate hydroxyaldehyde are possible. For example, hydroxypivaldehyde tends to decompose already at 130° C. Also harmful side reactions decrease as a result of lower hydrogenation temperature. The useful age of the hydrogenation catalyst is lengthened if the reaction mixture fed to hydrogenation does not contain triethylamine. Furthermore, in the process according to the invention the regeneration of the aldolisation catalyst is easy.

To achieve these advantages, this invention relates to a process for the preparation of polyvalent alcohols by hydrogenation of an aldehyde, in which process said aldehyde is obtained by aldolisation reaction of an aldehyde containing an α hydrogen atom and having the formula $R_1CHO$, or the mixture of said aldehyde with a second different aldehyde having the formula $R_2CHO$, wherein $R_1$ is selected from alkyl having 1–12 carbon atoms, cycloalkyl, aryl and aralkyl having 1–14 carbon atoms, and $R_2$ is selected from H, alkyl having 1–12 carbon atoms, cycloalkyl, aryl and aralkyl having 1–14 carbon atoms, and aldolisation being carried out in the presence of a weak base anion exchange resin, and the hydrogenation being carried out in the presence of a solvent and a hydrogenation catalyst.

DETAILED DESCRIPTION OF THE INVENTION

Ion exchange resins are classified into cation exchange resins, anion exchange resins and amphoteric ion exchange resins. Depending on the acidity or alkalinity of the ionogenic group, we speak of strongly or weakly acidic cation exchange resins and of strongly or weakly basic anion exchange resins.

Anion exchange resins have been developed considerably since 1947 when the first gel type resins having amine type functional group was introduced. Macroporous type resin was developed 1957 and first macroporous anion exchange resins were commercialized about 1960. Polyacryl amide as a matrix for weak anion exchange resin came into markets rather late during eighties.

Due to product developments the mechanical and thermal stability has improved considerably since 1960 to present. These changes have increased the usable lifetime. The guality of resins has improved ja the density of functional groups has increased. The modern weak anion exchange resins contain almost totally $-N(CH_3)_2$ groups, whereas during sixties weak anion exchange resins contained also a lot of strong $-N(CH_3)_3{}^+$ groups. Probably for this reasons weak anion exchage resins have not been considered usable in commercial aldolisation.

When polymers are used as matrices for catalysts, the activity and selectivity of the supported catalytic groups is greatly affected by so-called "polymer effects." Interaction between the polymer matrix and the surrounding affects the properties of the resin, and the reasons for this may be both physical and chemical.

Resin matrices are either of the gel-type or macroporous. The skeletal structure of a gel-type resin is obtained as a gel from polymerization. Gel-type resins do not have permanent porosity; they swell to varying degrees in polar solvents, which open their structure. The spaces between the cross bridges, filled with swelling solvent, can be viewed as being micropores. These spaces may contain solvent, but also semi-dissolved polymer segments. Mobility within the micropores is limited owing to the high viscosities of the solutions.

Macroporous resins have permanent internal porosity, and usually a higher degree of cross-bridging of the polymer is required for preventing collapse of the structure. Macroporosity leads to better transfer of material inside the particles, and thus often to a better reaction rate.

According to the invention it has been observed that both gel-like and macroporous weak base anion exchange resins can be used advantageously as catalysts in aldolisation. Weak anion exchange resins are mostly of the amine type. These include resins which have as functional groups a primary amine ($-NH_2$), a secondary amine ($-NHR$, where R may be, for example, an alkyl or aryl group) or a tertiary amine ($-NR_2$, where each R may be the same or different group, for example an alkyl or aryl group), or mixtures thereof. Strong anion exchange resins having a functional group of $-NR_3{}^+$ type are not usable because of low conversion of starting aldehyde.

The resin matrix used may be, for example, condensation products of epichlorohydrine with amine or ammonia, phenolic resins, acrylic resins, or styrene copolymers, such as chloromethylated styrene-divinylbenzene copolymer. Suitable as weak anion exchange resins are both anion exchange resins in which the resin matrix is gel-type and those in which the resin matrix is macroporous. In these resins the polymer matrix is an epoxy, acrylic, styrene or phenolic resin. The cross-bridging agent used in the polymer matrix is usually divinylbenzene.

The ion form of the resin is important. The ion form according to the invention must be $OH^-$ when functional group is charged. Otherwise functional group should be in free base form. Other ion forms like $CL^-$ have appeared to be ineffective.

Resins such as these, which are mostly used for the treatment of water, are marketed, for example, under the trade names of LEWATIT (manufacturer Bayer Ag); DOWEX (manufacturer Dow Chemical); DIAION, NEKROLITH and RELITE (manufacturer Mitsubishi Chemical); PUROLITE (manufacturer Purolite); AMBERLITE, AMBERLYST and DUOLITE (manufacturer Rohm and Haas); SERDOLIT (manufacturer Serva Heidelberg GmbH); IONAX (Manufacturer Sybron Chemicals Inc.); and FINEX (manufacturer Finex-FX Oy).

In one embodiment of the invention the first step in the process is the aldolisation reaction of an aldehyde containing a hydrogen atom in the presence of weak base anion exchange resins. Said aldehyde has a general formula of $R_1CHO$, where $R_1$ is selected from alkyl having 1–12 carbon atoms, cycloalkyl, aryl and aralkyl having 1–14 carbon atoms. The aldolisation reaction forms a reaction product mixture comprising or containing an aldol of said aldehyde, an unsaturated aldehyde derived by dehydration of said aldol, or mixtures thereof. The term "unsaturated aldehyde derived by dehydration of said aldol" refers to the α,β- olefinic aldehyde resulting from the dehydration of the aldol produced in the reaction.

In a second embodiment of the invention the first step in the process is the aldolisation reaction of aldehydes containing a mixture of an aldehyde containing α hydrogen atom defined above and a second different aldehyde having a general formula of general formula of $R_2CHO$, where $R_2$ is selected from H, alkyl having 1–12 carbon atoms, cycloalkyl, aryl and aralkyl having 1–14 carbon atoms, in the presence of weak base anion exchange resins.

Suitable starting aldehydes are, for example, formaldehyde, etanal, propanal, butanal, pentanal, 2-methylpropanal (isobutyraldehyde), 2-methylbutanal, 2-ethylpentanal, 2-ethylhexanal, 2-isopropylbutanal, 2-phenylpropanal, 2-cyclohexylpropanal, 2-phenylbutanal, 2,3-diphenylpropanal, cyclopentylaldehyde and cyclohexylaldehyde.

In one preferable embodiment of the invention the aldehyde containing α hydrogen atom is isobutyraldehyde and the second different aldehyde is formaldehyde. The expression "formaldehyde" comprises both conventional formaldehyde obtained as an aqueous solution and anhydrous forms of formaldehyde, such as paraformaldehyde and trioxane. Commercially available aqueous formaldehyde usually also contain relatively small amounts of methanol.

In the aldolisation step, for example, an aldehyde and formaldehyde are contacted with an anion exchange resin at a molar ratio of 15:1–1:15, preferably 5:1—1:5. The reaction may be carried out at a temperature of 15–100° C. The upper limit for the temperature is set by the thermal resistance of the anion exchange resin. The aldolisation reaction may be performed as a batch process or a semi-batch process, or preferably as a continuous process.

The catalyst may be mixed directly with the initial substances, or it may be tied in place by methods preventing the moving of the catalyst particles, methods which themselves do not pertain to the scope of the present invention. In view of a continuous process, the latter method is preferable, since in such a case the reaction mixture obtained after the aldolisation does not contain the aldolisation catalyst. In the former case, the catalyst must be separated from the reaction mixture by filtration or some other procedure before the hydrogenation.

Solvents may be used also in the aldolisation step in an amount of 0–50% by weight, preferably within a range of 0–30% by weight. The solvent swells the resin catalyst during the aldolisation and helps to keep the reaction mixture as single phase. Solvents have also a washing effect because they can wash impurities and residues from the resin and thus increase the usable lifetime of the resin. Suitable solvents include water and various alcohols and ketones, such as methanol, ethanol, 1-propanol, isopropanol, 1-butanol and isobutanol, or mixtures thereof.

The ion form of anion exchange resin has a great importance in view of catalytic activity. When anion exchange resins are used as an aldolisation catalyst the ion form of resin becomes unfavourable in the continuous use. Aldehydes as starting materials oxidate easily to corresponding carboxyl acids and carboxyl acids may form also as reaction products. Between carboxyl acids (RCOOH) and the functional group —$NR_2$ of the resin being in free base form an ion exchange reaction takes place:

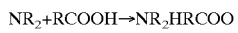

When the functional group is $NR_2HRCOO$ form it is no longer catalytically active. The resin can be regenerated easily back into —$NR_2$ form by periodically washing or flushing with alkaline solutions, for example NaOH solution.

After the aldolisation step and, when necessary, after the separation of the anion exchange resin, the reaction mixture is fed without any other separation steps directly to hydrogenation. In the hydrogenation it is possible to use as the catalyst preferably copper chromite and oxides of copper, cobalt, chromium, manganese, nickel and zinc or mixtures thereof. Catalysts based on platinum, ruthenium, rhodium, palladium or tungsten or mixtures thereof are also possible. It is further preferable to use these metals combined with a suitable carrier, such as carbon, silica, alumina or zeolites or mixtures thereof.

The hydrogenation is performed in solvents, which include alcohols, ketones and ethers, e.g. methanol, ethanol, propanol, isobutanol, hexanol, octanol, neopentyl glycol and butyl ether or dioxane. Preferable solvents are methanol, propanol and isobutanol. The amount of solvent may range from 1 to 70% by weight, but preferably from 10 to 50%. The most important role of the solvent is to decrease the rate of side reactions and to enable the use of hydrogenation temperature below the melting point of hydroxyaldehyde by dissolving the solid hydroxyaldehyde in the liquid phase.

The hydrogenation is preferably performed at an elevated temperature and pressure. The temperature may range from 50 to 200° C. preferably 70–120° C. and the hydrogenation pressure from 1 to 200 bar, preferably from 5 to 100 bar. Preferably solid-bed catalysts are used. The hydrogenation may be performed as a batch or semi-batch process, preferably as a continuous process.

After the hydrogenation reaction, the desired alcohol, for example, pentaerythritol, neopentyl glycol or trimethylolpropane, is separated from the reaction mixture by a suitable method, for example by distillation, and the solvents used may be recycled to the hydrogenation and/or aldolisation step.

The invention is described below in greater detail, with reference to the accompanying examples, which are not, however, intended as limiting the invention.

EXAMPLE 1

Hydroxypivaldehyde were prepared by using weak anion exchange resin (IRA 67) as catalyst in a continuous tube reactor.

Experiment arrangements were as follows:

| | |
|---|---|
| Reactor | Tube reactor (glass), length l = 70 cm, diameter d = 1.6 cm with cooling jacket |
| Catalyst | Amberlite IRA 67, volume V = 130 ml. |
| Feed | Mixture of formalin and IBAL in methanol, methanol content 12 wt % |
| Molar ratio IBAL/FA | 1.05 |
| Temperature | 60° C. |
| Pressure | 1 bar |
| Residence time | 7 h |
| Operation mode | Feed mixture is pumped continuously through the resin bed keeping the temperature constant, feed rate 18.6 ml/h. |

The analysed composition of the product mixture, 200 g, is shown in the following Table 1.

TABLE 1

| Compound | Product wt % |
|---|---|
| HPA | 61.6 |
| NPG | 0.25 |
| HPHP | 0.25 |
| NPG-mibut | 0.06 |
| IBAL | 4.34 |
| MeOH | 12.2 |
| IBUOH | — |
| H₂O | 19.4 |
| CHOOH | 0.06 |
| FA | 0.81 |
| Others | 0.94 |

Others includes unidentified components.

The following selectivity, conversion and yield values can be calculated based on formaldehyde, which is the limiting component.

HPA selectivity: 99.0% based on reacted formaldehyde HPA yield: 94.8% based on formaldehyde FA conversion: 95.8%.

EXAMPLE 2a

Aldolisation of formaldehyde and IBAL was carried out by the procedure according to Example 1. The catalyst was separated by filtration, and methanol in an amount of 51% by weight was mixed with the solution. The hydrogenation was performed feeding 160 g of the solution above into a batch-type Parr reactor having a volume of 300 ml by keeping constant hydrogen pressure 70 bar. The hydrogenation temperature was 140° C. and time was 120 min. The hydrogenation catalyst was copper chromite on alumina, total Cu content was 34 wt-%, Cr content 32 wt-%. The catalyst amount was 5.0 wt-% based on HPA amount.

EXAMPLE 2b (comparison)

The same experiment arrangement as in Example 2 was used in this example. The difference is the feed mixture, which contains TEA (triethylamine) as the aldolisation catalyst. Operating conditions were the same as in Example 2.

The composition of the feed and product mixtures in both examples are shown in the following Table 2. The NPG yield is indicated as the percentage share of the NPG amount formed in the hydrogenation of the HPA amount present in the feed stream. The NPG selectivity is indicated as the percentage share of the NPG formed in the hydrogenation of the reacted HPA. The conversion of HPA is indicated as the percentage share of the reacted HPA of the HPA amount present in the feed.

TABLE 2

| | Example 2a | | Example 2b (comparison) | |
|---|---|---|---|---|
| | Hyrogenation | | | |
| Compound | Feed wt % | Product wt % | Feed wt % | Product wt % |
| HPA | 34.4 | 0.71 | 29.3 | 0.83 |
| NPG | 0.18 | 33.6 | 1.84 | 25.6 |
| HPHP | 0.12 | 1.17 | 0.06 | 0.91 |
| NPG-mibut | 0.03 | 0.21 | 0.08 | 0.4 |
| IBAL | 1.7 | 0.04 | 4.7 | 0.53 |
| MeOH | 51.0 | 51.0 | 46.6 | 46.7 |
| IBUOH | — | 2.87 | — | 5.8 |
| H₂O | 10.3 | 10.3 | 13.0 | 13.0 |
| TEA | — | — | 3.1 | 2.82 |
| HCOOH | 0.03 | 0.03 | 1.1 | 0.34 |
| Others | 2.2 | 0.1 | 0.17 | 3.0 |

HPA = hydroxypivaldehyde, NPG = neopentyl glycol, HPHP = hydroxypivalyl hydroxypivalate, NPG-mibut = NPG-monoisobutyrate, IBAL = isobutyraldehyde, MeOH = methanol, IBUOH = isobutanol, HCOOH = formic acid, others = formaldehyde and unidentified components, TEA = triethylamine In example 2a the NPG selectivity was 90.7% and HPA conversion was 98.1%. In comparison example 2b the corresponding values were 87.7% and 97.0%.

The results indicate that higher NPG selectivity and thus better utilisation of raw materials is achieved when ion-exchange resin is used as aldolisation catalyst in the NPG manufacturing process.

EXAMPLE 3

61.83 g of formaldehyde and 75.01 g of isobutyraldehyde were reacted by the procedure according to Example 1. The catalyst was 41.61 g of AMBERLITE IRA-93, which is a macroporous weak anion exchange resin. The reaction temperature was 60° C., and IBAL was added in the course of 1.4 hours. The results are presented in Table 3 below.

TABLE 3

| Compound | Products after IBAL-addition (wt %) | Products 2 h after IBAL-addition (wt %) |
|---|---|---|
| HPA | 25.6 | 41.7 |
| IBAL | 27.4 | 17.2 |
| Water | 23.0 | 23.0 |
| NPG | 0.0 | 0.0 |
| Formic acid | 0.4 | 0.0 |
| Isobutyric acid | 2.5 | 0.07 |
| HPAA | 0.2 | 0.0 |
| HPHP | 0.2 | 0.0 |
| Methanol | 0.2 | 0.22 |
| Others (e.g. unreacted formaldehyde) | 20.5 | 17.8 |

IBAL conversion (2 hours after IBAL addition) was 68.5% and HPA selectivity was 100.0%.

Aldolisation works also with different type of resin (IRA-93) though reaction rate is lower than with acrylamide resin IRA-68.

EXAMPLE 4

An aldolisation tests were carried out in tubular reactor by using weak and strong anion exchange resins as catalyst, the residence time of 1.5 h, the temperature of 60° C. and the mole ratio IBAL/CH₂O of 1:1. The matrix of both resins was a gel type polystyrene cross-linked with divinylbenzene.

The weak anion exchange resin was Diaion WA10 (Mitsubishi Chemical Corp), the functional groups of which were —N(CH$_3$)$_2$ type. The strong anion exchange resin was Amberlite IRA-400 (Rohm and Haas Company), the functional groups of which were —N(CH$_3$)$_3$+ type. The ion form of both resins was OH$^-$. Product sample for analysis was taken after the reaction time of 6 hours.

The results are presented in Table 4 below.

TABLE 4

| Resin | IBAL-conversion (%) | HPA-selectivity (%) |
|---|---|---|
| Weak base anion exchange resin | 42.2 | 99.5 |
| Strong base anion exchange resin | 6.3 | 91.3 |

The results presented in Table 4 show that it is advantageous to use weak base anion exchange resin having tertiary amine —NR$_2$ as functional group instead of strong base anion exchange resin having the group —NR$_3$$^+$ as functional group. Also weak anion exchange resins having primary group —NH$_2$ or secondary group —NHR are not usable because they inactivate rapidly under synthesis conditions.

EXAMPLE 5

Aldolisation tests were carried out in a tubular reactor by using weak anion exchange resin as a catalyst, the residence time of 2 h, the temperature of 60° C. and the mole ratio IBAL/CH$_2$O of 1:1. All resins were weak base anion exchange resins having a functional group of —N(CH$_3$)$_2$. Several matrices were used: polyacryl amide cross-linked with divinylbenzene (Amberlite IRA-67, Rohm and Haas Company), polystyrene cross-linked with divinylbenzene (Amberlite IRA-96, Rohm and Haas Company), epoxy resin (Dovex WGR-2, Dow Chemical Co) and phenol-formaldehyde resin (Duolite A-7, Rohm and Haas Company). The ion form in all resins was OH$^-$. Product sample for analysis was taken after the reaction time of 6 hours. The results are presented in Table 5 below.

TABLE 5

| Resin matrix | IBAL-conversion (%) | HPA-selectivity (%) |
|---|---|---|
| Polyacryl-DVB | 76.7 | 99.8 |
| Polystyrene-DVB | 45.4 | 99.5 |
| Epoxy resin | 39.2 | 99.6 |
| Phenol formaldehyde | 5.2 | 95.2 |

Especially advantageous is a weak anion exchange resin having a matrix of polyacryl resin cross-linked with divinylbenzene.

EXAMPLE 6

Aldolisation tests were carried out in tubular reactor by using weak and strong anion exchange resin as a catalyst, the residence time of 2 h, the temperature of 60° C. and the mole ratio IBAL/CH$_2$O of 1:1. The anion exchange resin was Amberlite IRA-67, in which the functional groups were —N(CH$_3$)$_2$ type and as the matrix polyacryl amide resin cross-linked with divinylbenzene. The ion form of resins were free base and Cl$^-$.

The results are presented in Table 6 below.

TABLE 6

| | IBAL-conversion (%) | HPA-selectivity (%) |
|---|---|---|
| Ion form free base | 76.7 | 99.8 |
| Ion form Cl | 3.5 | 91.2 |

In the aldolisation reaction it is advantageous to use anion exchange resin having an ion form of free base or OH instead of Cl$^-$. Anion exchange resins having other ion form have no effect on aldolisation reaction.

EXAMPLE 7

The aldolisation reaction was carried out as in Example 6 but using two different weak anion exchange resins having a functional group —N(CH$_3$)$_2$ as the catalyst. The matrices were gel-type (AMBERLITE IRA-67), Rolhm and Haas Company) and macroporous-type (PUROLITE A835, The Purolite Company).

The results are presented in the Table 7 below.

TABLE 7

| Matrix | IBAL-conversion (%) | HPA-selectivity (%) |
|---|---|---|
| Gel-type | 76.7 | 99.8 |
| Macropous type | 86.3 | 99.6 |

The resins prepared from the same material can vary depending on the naure of the matrix.

EXAMPLE 8

Propionaldehyde and formaldehyde were reacted in water-methanol solution with ion exchange resin IRA 67 as the catalyst. Formaldehyde was used in excess (20–25% above the stoichiometric amount). The initial temperature was 50° C. and it increased about 10° C. during the reaction. The results are presented in Table 8 below.

TABLE 8

| Experiment | MeOH wt % | PAL wt % | conv. (5 h) % | select. (5 h) % | select. (70%) % |
|---|---|---|---|---|---|
| 1 | 0.5 | 25 | 92 | 38 | 32 |
| 2 | 7 | 21 | 84 | 39 | 35 |
| 3 | 11 | 20 | 76 | 36 | 33 |

MeOH = methanol concentration at start
PAL = propionaldehyde concentration at start
conv. (5 h) = propionaldehyde conversion after 5 h of reaction
select. (5 h) = dimethylolpropionaldehyde selectivity after 5 h of reaction calculated from the reacted propionaldehyde
select. (70 %) = dimethylolpropionaldehyde selectivity calculated from the reacted propionaldehyde at 70% propionaldehyde conversion The results indicate that small amounts of methanol decrease propionaldehyde conversion but do not affect selectivity to dimethylolpropionaldehyde.

EXAMPLE 9

Propionaldehyde and formaldehyde were reacted in water-alcohol solution with ion exchange resin IRA 67 as the catalyst. Formaldehyde was used in excess (25% above the stoichiometric amount). The initial temperature was 50° C. and it increased 6° C. during the reaction. The results are presented in Table 9 below.

TABLE 9

| Experiment | MeOH wt % | IPA wt % | PAL wt % | conv. (5 h) % | select. (5 h) % | select. (70%) % |
|---|---|---|---|---|---|---|
| 4 | 32 | 0 | 15 | 30 | 14 | 14 |
| 5 | 5 | 27 | 15 | 54 | 30 | 19 |

The results indicate that when methanol is replaced by isopropanol, higher conversion and selectivity are obtained.

EXAMPLE 10

The aldolisation reaction was performed in a glass reactor having a total volume of 0.8 dm$^3$. The reactor was equipped with a stirrer having a rotation velocity of 500 min$^{-1}$. The heating of the reactor was carried out using a thermostat-controlled water jacket, and the temperature was maintained constant during the reaction.

The initial substances, 2-ethylhexanal (2-EHAL) and formaldehyde (37%), were placed in the reactor and were allowed to reach the reaction temperature while the mixture was stirred. The reaction was started by adding the ion-exchange catalyst into the reactor. When the reaction samples were taken, the stirring was stopped, the phases were allowed to separate for 1 min, and a sample was taken from the organic phase. The mass of the organic phase was weighed after a trial run. The molar ratio of 2-EHAL to formaldehyde was 1:1.5 in all of the runs. The conditions are shown in Table 10a, and the composition of the organic phase after a run of 8 hours is shown in Table 10b.

TABLE 10A

| Run | 2-EHAL (g) | Formal-dehyde (g) | Temperature ° C. | Catalyst | Catalyst amount (g) |
|---|---|---|---|---|---|
| 1 | 165.7 | 159.1 | 60 | IRA-93 | 22.8 |
| 2 | 164.3 | 160.1 | 80 | IRA-93 | 22.8 |
| 3 | 164.5 | 159.7 | 50 | IRA-68 | 22.8 |
| 4 | 165.3 | 159.5 | 60 | IRA-68 | 22.8 |
| 5 | 164.0 | 160.2 | 60 | IRA-68 | 68.4 |

TABLE 10B

| Run | 2-EHAL conversion % | BEPD-aldol selectivity % |
|---|---|---|
| 1 | 1 | 35.0 |
| 2 | 7.9 | 65.4 |
| 3 | 6.2 | 66.7 |
| 4 | 23.6 | 51.3 |
| 5 | 72.5 | 44.0 |

EXAMPLE 11

The effect of the solvent amount on the selectivity of the hydrogenation of HPA to NPG was examined in this example. The crude HPA was prepared using a weak anion exchange resin as aldolisation catalyst. The experiment arrangement are give below.

Reactor: Parr 300 ml with spinning catalyst basket
Catalyst: Ni on silica, total Ni content 73 wt-% (Ni, NiO)
Feed: Crude HPA from aldolisation without any purification, batch totally 160 g
Solvent: methanol
Catalyst/HPA-ratio: constant 5.5 wt-% catalyst based on HPA amount
Temperature: 100° C.
Pressure: 70 bar (abs)
Reaction time: 120 min
Solvent amount: 0, 20, 40 wt-% based on the hydrogenation feed mixture
Operation mode: batch process keeping the hydrogen pressure constant The results presented in Table 11 below show that the effect of solvent (methanol) on the selectivity of NPG is increasing when the amount of solvent methanol is increased:

TABLE 11

| Methanol (wt %) | Selectivity (%) |
|---|---|
| 0 | 80.5 |
| 20 | 84.3 |
| 40 | 93.3 |

The increasing amount of the solvent methanol decreased also the formation rates of the by-products HPHP and NPG-monoisobutyrate thus increasing the overall selectivity of the hydrogenation of HPA to NPG.

EXAMPLE 12

The applicability of other solvents to be used in the hydrogenation of HPA to NPG was examined in this Example. Isobutanol was used as solvent in the hydrogenation.

The experiment arrangement is given below:

Reactor: Parr 300 ml with spinning catalyst basket
Catalyst: Ni on silica, total Ni content 69 wt-% (Ni,NiO), Cr content 13 wt-%
Feed: Crude HPA from aldolisation without any purification, batch totally 160 g
35 Solvent: Main solvent isobutanol, also 7 wt-% MeOH present in the mixture
Catalyst/HPA-ratio: constant 5.5 wt-% catalyst based on HPA amount
Temperature: 100° C.
Pressure: 70 bar (abs)
Reaction time: 180 min
Solvent amount: iBUOH and MeOH totally 50 wt-% in the reaction mixture
Operation mode: Batch process keeping the hydrogen pressure constant The composition of the feed and product mixtures are shown in the Table 12.

TABLE 12

| Compound | Feed wt % | Product wt % |
|---|---|---|
| HPA | 36.2 | 0.1 |
| NPG | 0.1 | 35.5 |
| HPHP | 0.1 | 0.46 |
| NPG-mibut | 0.02 | 0.1 |
| IBAL | 2.4 | 0.01 |
| MeOH | 6.8 | 7.3 |

TABLE 12-continued

| Compound | Feed wt % | Product wt % |
|---|---|---|
| IBUOH | 43.6 | 45.8 |
| H₂O | 10.8 | 10.8 |

HPA = hydroxypivaldehyde, NPG = neopentyl glycol, HPHP = hydroxypivalyl hydroxypivalate, NPG-mibut = NPG-monoisobutyrate, IBAL = isobutyraldehyde, MeOH = methanol, IBUOH = isobutanol The NPG-selectivity was 98.3% and HPA-conversion was 99.7%.

The result indicates that isobutane is suitable solvent to be used in the hydrogenation.

EXAMPLE 13

Weak anion exchange resin (Amberlite IRA 67, manufactured by Rohm & Haas) was used as aldolisation catalyst for producing hydroxypivaldehyde from formaldehyde and isobutyraldehyde. Methanol was added into reaction mixture for producing a feed material for hydrogenation having the properties in the Table 13a below:

TABLE 13A

| Compound | wt % |
|---|---|
| CH₂O | 0.53 |
| IBAL | 4.08 |
| H₂O | 11.5 |
| MeOH | 52.9 |
| HPA | 30.8 |
| NPG | 0.07 |
| HPHP | 0.06 |
| HCOOH | 0.01 |
| HPAA | 0.05 |
| NPG-isobut. | 0.02 |

The following hydrogenation catalysts were tested. NPG-selectivity, NPG-yield and HPA-conversion were calculated to compare the performance of each catalyst. NPG-yield:

Catalyst 1: Ni on silica, total Ni 73 wt-%

Catalyst 2: Ni on silica, total Ni 78 wt-%

Catalyst 3: Ni on silica, MgO promoted, total Ni 74 wt-%

Catalyst 4: Ni on silica, total Ni 78 wt-%

Catalyst 5: Ni (69 wt-%)/Cr (13 wt-%) on silica

Catalyst 6: CuCr on alumina, Ba promoted, total Cu 34 wt-%,Cr 32 wt-%

Catalyst 7: CuZn on alumina, Cu 25 wt-%, Zn 33.5 wt-%

Catalyst 8: Ni on alumina, Ni 20 wt-%

All catalysts were crushed and screened to particle size 1.0–1.4 mm. Hydrogenation was carried out in Parr-reactor with spinning basket and mixing baffles. The catalysts were activated by heating one hour at 170° C., hydrogen pressure 2 bar (abs.), except catalysts 8, where the activation temperature was 250° C. The hydrogenation pressure was 70 bar and hydrogenation time was 180 min. The hydrogenation temperature was 100° C., except for catalysts 6 and 7, where 140° C. was used.

The results are presented in Table 13b below.

TABLE 13B

| Catalyst | NPG-selectivity % | HPA-conversion % | NPG-yield % |
|---|---|---|---|
| Catalyst 1 | 84.6 | 99 | 83.8 |
| Catalyst 2 | 95.8 | 94.3 | 90.3 |
| Catalyst 3 | 98.4 | 99.7 | 98.1 |
| Catalyst 4 | 97.8 | 99 | 96.8 |
| Catalyst 5 | 98.8 | 99.4 | 98.2 |
| Catalyst 6/100° C. | 98.2 | 94 | 92.3 |
| Catalyst 6/140° C. | 97.1 | 99.4 | 96.5 |
| Catalyst 7/100° C. | 81.3 | 55.1 | 44.8 |
| Catalyst 7/140° C. | 85.6 | 99 | 84.7 |
| Catalyst 8 | 88.9 | 40.8 | 36.3 |

The selectivity and conversion calculations are based on the analysis of the hydrogenation product mixture. Liquid chromatography was used to analyse FA, HPA, HPHP, HCOOH and HPAA, gas chromatography was iUsed to analyse IBAL, MeOH, NPG and NPG-isobutyrate.

The most selective catalyst for NPG production at high conversion level are the two Ni-catalyst on silica support, catalyst 3 and catalyst 5. Also catalyst 6 (CuCr on alumina) gave reasonable good results at the higher temperature (140° C.), but catalyst 8 (Ni on alumina) showed poor activity although also a higher temperature (250° C.) was used during the activation of this catalyst.

EXAMPLE 14

Example 6 was repeated by using a residence time of 1.5 hours. From the outlet of the reactor samples were taken 8 hours and 72 hours after the starting of the reaction. Then the resin was regenerated by introducing water solution of NaOH (1-M) through the resin bed. The reaction was started again and a sample was taken after 8 hours from the starting of the reaction.

The results are presented in Table 14 below.

TABLE 14

| Sample | IBAL-conversion (%) | HPA-selectivity (%) |
|---|---|---|
| 8 hours | 74.7 | 99.8 |
| 72 hours | 58.7 | 99.8 |
| 8 hours after regeneration | 73.5 | 99.8 |

The results indicate that resin catalyst can be easily regerated to original conditions.

EXAMPLE 15

The hydrogenation of HPA to NPG was examined in methanol solvent. The experiment arrangement is given below:

Reactor: Parr 300 ml with spinning catalyst basket

Catalyst Ni on silica, total Ni content 69 wt-% (Ni,NiO), Cr content 13 wt-%, 26.7 g Feed: Crude HPA from aldolisation without any purification, batch totally 160 g Solvent: Methanol Temperature: 70° C.

Pressure: 70 bar (abs)

Reaction Time: 240 min

Operation mode: Batch process keeping the hydrogen pressure constant

The composition of the feed and product mixtures are shown in the Table 15.

TABLE 15

| Compound | Feed wt % | Product wt % |
|---|---|---|
| HPA | 33.0 | 3.0 |
| NPG | 0.08 | 30.5 |
| HPHP | 0.08 | 0.17 |
| NPG-mibut | 0.04 | 0.06 |
| IBAL | 4.34 | 0.11 |
| MeOH | 50.4 | 50.0 |
| IBUOH | — | 4.21 |
| H$_2$O | 11.8 | 11.8 |
| Others | 0.26 | 0.15 |

HPA = hydroxypivaldehyde, NPG = neopentyl glycol, HPHP = hydroxypivalyl hydroxypivalate, NPG-mibut = NPG-monoisoburyrate, IBAL = isobutyraldehyde, MeOH = methanol, IBUOH = isobutanol, Others = formaldehyde and unidentified components The NPG-selectivity was 98.5% and HPA-conversion was 91% based on product analysis.

The results indicates that use of solvent makes possible to hydrogenate at low temperatures the amount of side products being very small.

What is claimed is:

1. A process for the preparation of polyvalent alcohols by hydrogenation of an aldehyde, which comprises:
   conducting an aldolisation reaction to obtain an aldehyde containing an α hydrogen atom and having the formula R$_1$CHO, or a mixture of said aldehyde with a second different aldehyde having the formula of R$_2$CHO, wherein R$_1$ is selected from alkyl having 1–12 carbon atoms, cycloalkyl, aryl and aralkyl having 1–14 carbon atoms, and R$_2$ is selected from H, alkyl having 1–12 carbon atoms, cycloalkyl, aryl, and aralkyl having 1–14 carbon atoms, wherein the aldolisation reaction is carried out in the presence of a weak base anion exchange resin at a temperature of 50 to 80° C.; and
   conducting a hydrogenation reaction on the aldehyde to prepare a polyvalent alcohol, wherein the hydrogenation reaction is carried out in the presence of a solvent and a hydrogenation catalyst.

2. A process according to claim 1, wherein the solvent is an aliphatic alcohol or ether.

3. A process according to claim 2, wherein the solvent is methanol, ethanol, n-propanol, isopropanol, n-butanol or isobutanol, or mixtures thereof.

4. A process according to claim 1, wherein the solvent is used in an amount of 1–70% by weight of the reaction mixture going to hydrogenation.

5. A process according to claim 1, wherein the anion exchange resin is an amine derivative of a chloromethylated styrene-divinylbenzene copolymer.

6. A process according to claim 1, wherein the anion exchange resin is an amine derivative of an acrylic polymer.

7. A process according to claim 1, wherein the anion exchange resin is an amine derivative of an epoxy or a phenolic resin.

8. A process according to claim 1, wherein the solvent is used in aldol reaction.

9. A process according to claim 8, wherein the amount of said solvent is at least 7 wt-%.

10. A process according to claim 1, wherein said aldehyde containing an a α hydrogen atom is butyraldehyde.

11. A process according to claim 1, wherein said aldehyde containing an α hydrogen atom is butyraldehyde and said second different aldehyde is formaldehyde.

12. A process according to claim 1, wherein the aldolisation reaction product is fed directly to hydrogenation without separation of unreacted formaldehyde or aldehyde.

13. A process according to claim 1, wherein the molar ratio of formaldehyde to aldehyde in the aldolisation is 15:1–1:15.

14. A process according to claim 1, wherein the hydrogenation is carried out at a temperature between 50–200° C.

15. A process according to claim 1, wherein one or more starting aldehydes are selected from the group of formaldehyde, ethanal, propanal, butanal, pentanal, 2-methypropanal (isobutyraldehyde), 2-methylbutanal, 2-ethylpentanal, 2-ethylhexanal, 2-isopropylbutanal, 2-phenylpropanal, 2-cyclohexylpropanal, 2-phenylbutanal, 2,3-diphenylpropanal, cyclopentylaldehyde, cyclohexylaldehyde and mixtures thereof.

16. A process according to claim 1, wherein said aldehyde is a mixture of isobutyraldehyde and formaldehyde and the final product is neopentyl glycol.

17. A process according to claim 1, wherein the hydrogenation catalyst contains metals or metal oxides selected from Cu, Co, Cr, Mn and Ni or mixtures thereof.

18. A process according to claim 1, wherein the catalyst also contains metals selected from chromium, magnesium, barium or zinc and mixtures thereof.

19. A process according to claim 1, wherein the hydrogenation catalyst used is a catalyst which contains platinum, ruthenium, palladium, rhodium and tungsten or mixtures thereof.

20. A process according to claim 17, wherein the hydrogenation catalyst contains an inert carrier material selected from carbon, silica, alumina, zeolites or mixtures thereof.

21. A process according to claim 1, wherein the solvent is used in an amount of 10–50% by weight of the reaction mixture going to hydrogenation.

22. A process according to claim 1, wherein the hydrogenation is carried out at a temperature between 70–120° C.

* * * * *